United States Patent [19]
Datar et al.

[11] Patent Number: 5,340,536
[45] Date of Patent: Aug. 23, 1994

[54] METHOD AND APPARATUS FOR NEUTRALIZATION OF BIOHAZARDOUS WASTE

[75] Inventors: Rajiv V. Datar, Glen Cove; Luis G. Rios, Holtsville, both of N.Y.

[73] Assignee: 3-I Systems, Plainsboro, N.J.

[21] Appl. No.: 993,944

[22] Filed: Dec. 18, 1992

[51] Int. Cl.$^5$ .............. A61L 2/08; B01J 3/04
[52] U.S. Cl. .................... 422/23; 422/26; 422/295; 422/308; 422/309; 219/688
[58] Field of Search ............ 422/22, 23, 26, 287, 422/295, 307–309, 900, 184, 186.29; 219/10.55 R, 10.81, 10.57; 250/455.11; 241/606

[56] References Cited

U.S. PATENT DOCUMENTS

| | | | |
|---|---|---|---|
| 3,589,276 | 6/1971 | Swallert | 241/606 X |
| 4,546,226 | 10/1985 | Trembley et al. | 219/10.81 |
| 4,861,956 | 8/1989 | Courneya | 219/10.55 R XR |
| 5,035,367 | 7/1991 | Nojima | 241/606 X |
| 5,106,594 | 4/1992 | Held et al. | 422/23 X |
| 5,119,994 | 6/1992 | Placzek | 422/26 X |
| 5,130,092 | 7/1992 | Liu | 422/28 |
| 5,185,126 | 2/1993 | Adamski et al. | 422/307 X |

FOREIGN PATENT DOCUMENTS

92/12738  8/1992  World Int. Prop. O. ............ 422/26

*Primary Examiner*—Robert J. Warden
*Assistant Examiner*—E. Leigh Dawson

[57] ABSTRACT

An apparatus and method for processing biohazardous wastes is disclosed. Biohazardous wastes are mechanically destroyed and neutralized with radio-frequency electromagnetic radiation and high-temperature steam inside an apparatus having a pressurized neutralization chamber.

31 Claims, 7 Drawing Sheets

METHOD AND APPARATUS FOR NEUTRALIZATION OF BIOHAZARDOUS WASTE

FIELD OF THE INVENTION

The invention relates to methods and apparatus for disposal of biohazardous waste. More particularly, the invention relates to methods and apparatus for neutralization of waste materials by steam and RF radiation.

BACKGROUND OF THE INVENTION

Biohazardous waste is any by-product of a biological, organic, pathological, or pharmaceutical process or method with the potential to endanger the health of humans and other life forms through infection or other means. Thus, "biohazardous" is broader in meaning than "infectious" or "infectious medical". For example, biohazardous waste encompasses organic wastes such as pharmaceutical waste, veterinary waste, food waste, and medical wastes.

Medical infectious waste is a serious concern because it can infect humans with deadly organisms such as the AIDS and hepatitis viruses. Such infectious waste is generated by hospitals and medical and veterinary care facilities as a by-product of their health and laboratory services. Due to the public awareness raised by AIDS, many have expressed concerns about unregulated and unauthorized disposal of medical waste.

The prior art has attempted to address the problem of disposing of medical waste by methods such as specialized land filling, incineration, steam autoclaving, ETO gas exposure, chemical treatment, radiation exposure (Gamma), microwave heating, and radio-frequency (RF) or dielectric heating. Incineration currently is the most popular method employed to dispose of medical and veterinary waste. However, incineration may produce gaseous emissions that may contain high levels of toxic heavy metals, e.g. cadmium, chromium, lead, mercury, dioxins and furans generated by the plastics and metallic content derived from syringes, needles, and sharps included in the waste.

Steam autoclaving is another known method for treating medical waste. Steam autoclaving is a thermal process in which the wastes are sterilized by exposure to high-temperature steam. The high temperature and good penetrability of steam effectively destroys the infectious agents. Since the waste is rendered sterile, it can be directly landfilled. However, for steam autoclaving to be an effective treatment method, the steam must fully penetrate the waste to guarantee that all infectious microorganisms are killed. Also, since autoclaved waste is neither mechanically destroyed nor significantly reduced in volume, it is still recognizable as medical waste.

U.K. Pat. No. 2,232,594 to Goldher et. al. and PCT application No. US91/02451 to Mertsch et. al. teach a process and apparatus for disinfecting medical waste using a combination of steam preheating, microwave heating, and conventional methods of conduction heating. The major drawbacks of these methods relate to the complexity and inefficiency of the plants due to the numerous heating methods and microwave energy sources required, as well as lack of control of steam formation during heating. For example, Mertsch et. al. requires pretreating the waste by exposure to steam and that the steam should be used to "build up overpressure" in the microwave chamber containing the waste for faster heating of the waste. Goldner et. al. requires use of a "temperature maintenance chamber" to supplement the heating produced by the microwave sources and to prevent the waste from "cooling". Also, since neither of these approaches control moisture content of the air, excessive steam formation can cause inefficient use of the microwave energy. In addition, microwave heating of medical waste has the disadvantage that the short wavelengths of microwaves limit their penetration. In contrast, the radio-frequency (RF) waves employed in the present invention have longer wavelengths, and penetrate more effectively.

U.S. Pat. No. 5,106,594 discloses disinfecting and processing medical waste by RF radiation and converting the disinfected waste into reclaimed plastic or low-sulfur fuel. The apparatus of U.S. Pat. No. 5,106,594 breaks up the waste into fragments, compresses the waste fragments to achieve volume reduction, disinfects the compressed waste fragments using a dielectric heater, and converts the disinfected waste into useful material by using reclamation equipment. A drawback of this method and apparatus, however, is that the medical waste is only disinfected rather than sterilized. Also, the method is time-consuming because after the waste is heated in the RF chamber, at least one hour of standing time is required outside the RF chamber to achieve a safe level of disinfection. The present invention, however, typically achieves neutralization in about $\frac{1}{3}$ the time required by the art.

Although the prior art devices provide for waste disposal, a long-term solution to the medical waste disposal problem must address and satisfy basic requirements. Medical waste disposal must be safe, efficient, and should reduce, if not completely eliminate, the risk of infection to humans. A need therefore exists for a method and apparatus for neutralizing or destroying the infectious potential of biohazardous waste, in particular, medical waste, and to transform it into a material which does not adversely impact the environment.

SUMMARY OF THE INVENTION

The present invention advantageously provides a method and an apparatus for processing biohazardous wastes, including medical waste, veterinary waste, and food waste, in a closed, continuous, and controllable manner. The invention changes the waste into fragments and then exposes the fragments to a thermal neutralization process involving radio-frequency (RF) radiation and high-temperature steam. The invention also advantageously provides continuous validation of all steps of the waste treatment process.

In accordance with the invention, a method and apparatus for neutralizing biohazardous waste is provided. The terms "neutralizing", "neutralized", and the like, as employed herein, is meant to encompass both disinfecting as well as sterilizing. Sterilizing is meant to provide for substantially 100% elimination of bacteria and other contagion such as as viruses. Sterilizing therefore substantially eliminates the risk of infection from the treated biohazardous waste. Disinfecting, however, is meant to provide elimination of sufficient bacteria and contagion sufficient to substantially reduce but not eliminate the risk of subsequent infection from the treated biohazardous waste. Selection of temperatures, pressures, radio frequency and intensity, as well as time of exposure can readily be varied in accordance with the invention to obtain sterilization or disinfection as desired.

The method of the invention entails subjecting the biohazardous waste to super heated steam and radio frequency (RF) radiation for sufficient time to neutralize the waste. The super heated steam and RF radiation may be applied to the waste simultaneously, and the waste may be maintained under a super atmospheric pressure prior to treating the waste with steam and RF radiation. The super atmospheric pressures may vary from 15-18 psig, the temperature of the steam may vary from 132° C.-171° C., and the RF radiation may vary from 1-200 mHz.

The method of the invention is performed with an apparatus that comprises, in combination, a fluid tight chamber for receiving biohazardous waste such as medical waste, a means for introducing the waste into a neutralization chamber, a means for producing super heated steam into the neutralization chamber, and means for subjecting the waste to RF radiation to enable the steam and RF radiation to neutralize the waste.

The apparatus of the invention may further include means to detect radioactive materials in the biohazardous waste as well as means for preventing fluid and solid contaminants in the waste from escaping the apparatus. The means to prevent the solid and fluid contaminants from escaping the apparatus includes a means to generate a negative atmospheric pressure in the loading chamber.

A means for sensing the temperature of the waste materials in the neutralization chamber is provided. Sensors can be employed to gauge the rate of loading of biohazardous waste into the loading chamber, the rate of shredding of the waste in the shredders, and the rate of loading of shredded biohazardous waste into the neutralization chamber.

The means for shredding the waste can achieve an 80% volume reduction of the waste material. The means for transporting the waste into the chamber can be a pneumatic conveyor that transports the waste by use of a high velocity air flow.

The neutralization chamber employed in the apparatus of the invention comprises a cyclone cavity that can be positioned above a radio-frequency heater applicator. The cyclone cavity has substantially parabolic and convex surfaces to separate the waste from the influx of air and waste which is introduced into the neutralization chamber.

The radio-frequency heater applicator employed in the invention comprises an outer, cylindrically-shaped tube that functions as a ground electrode. An inner, cylindrically-shaped rod is centrally disposed in and concentric with the outer tube to form the heater electrode of the RF applicator. A solid circular slab may be positioned at the bottom of the neutralization chamber to function as an insulator for the RF heater applicator. The slab is sufficiently thick to prevent radio-frequency energy from leaking from the neutralization chamber.

The ground electrode of the RF applicator comprises an outer tubular shell, an inner tubular shell, and a middle tubular shell disposed between the inner and outer shells. The middle shell is composed of an electrically conductive metal such as aluminum or copper. The heater electrode of the RF applicator is formed of an outer structural tube formed of a dielectric insulating material, an inner conductor tube connected to a source of radio-frequency electricity, and a passageway inside the conductor tube for passing coolant fluid electrode.

DETAILED DESCRIPTION OF THE INVENTION

Figure 1:
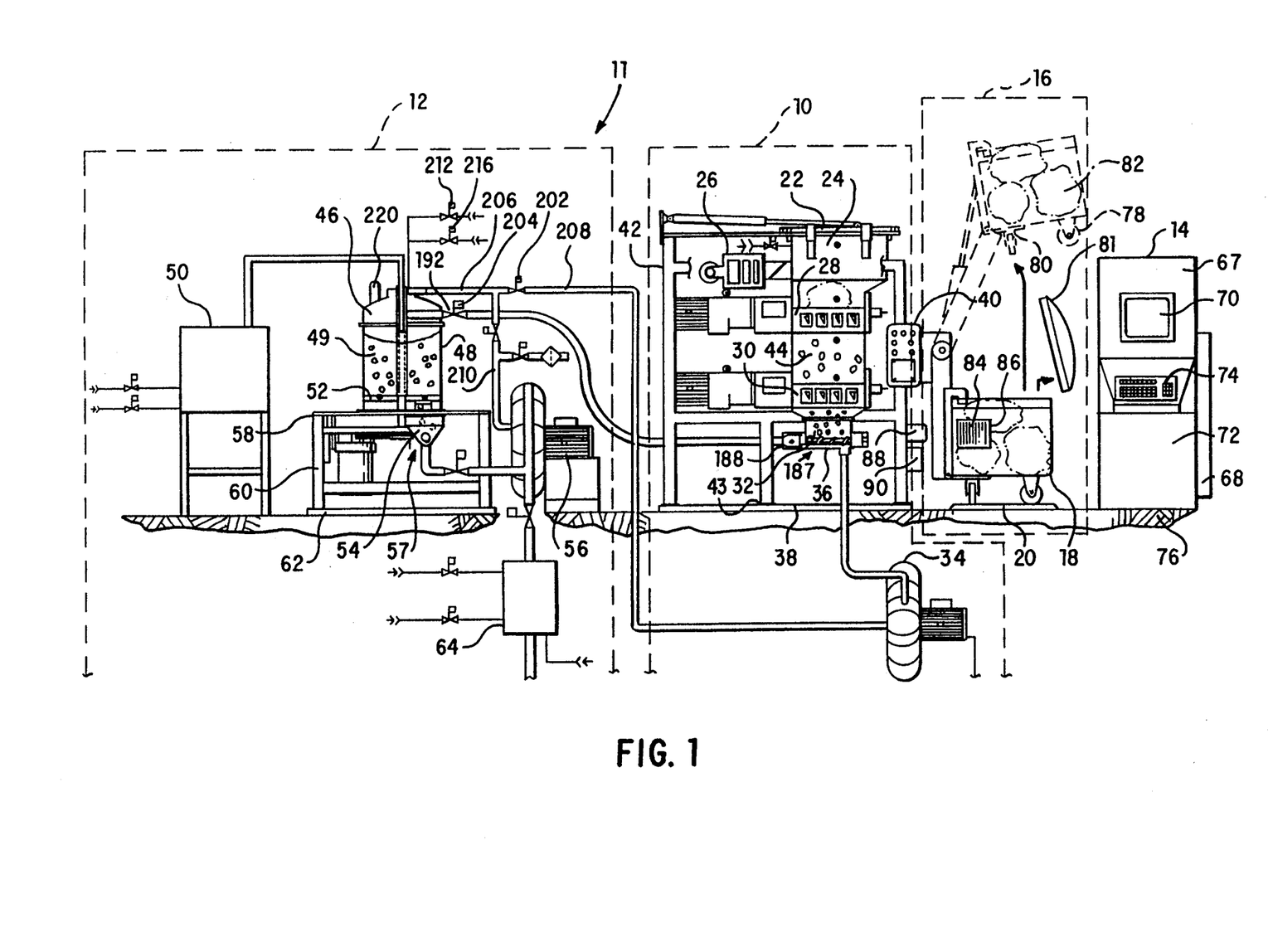
FIG. 1 is a front elevational view of the apparatus of the invention.
Figure 2:
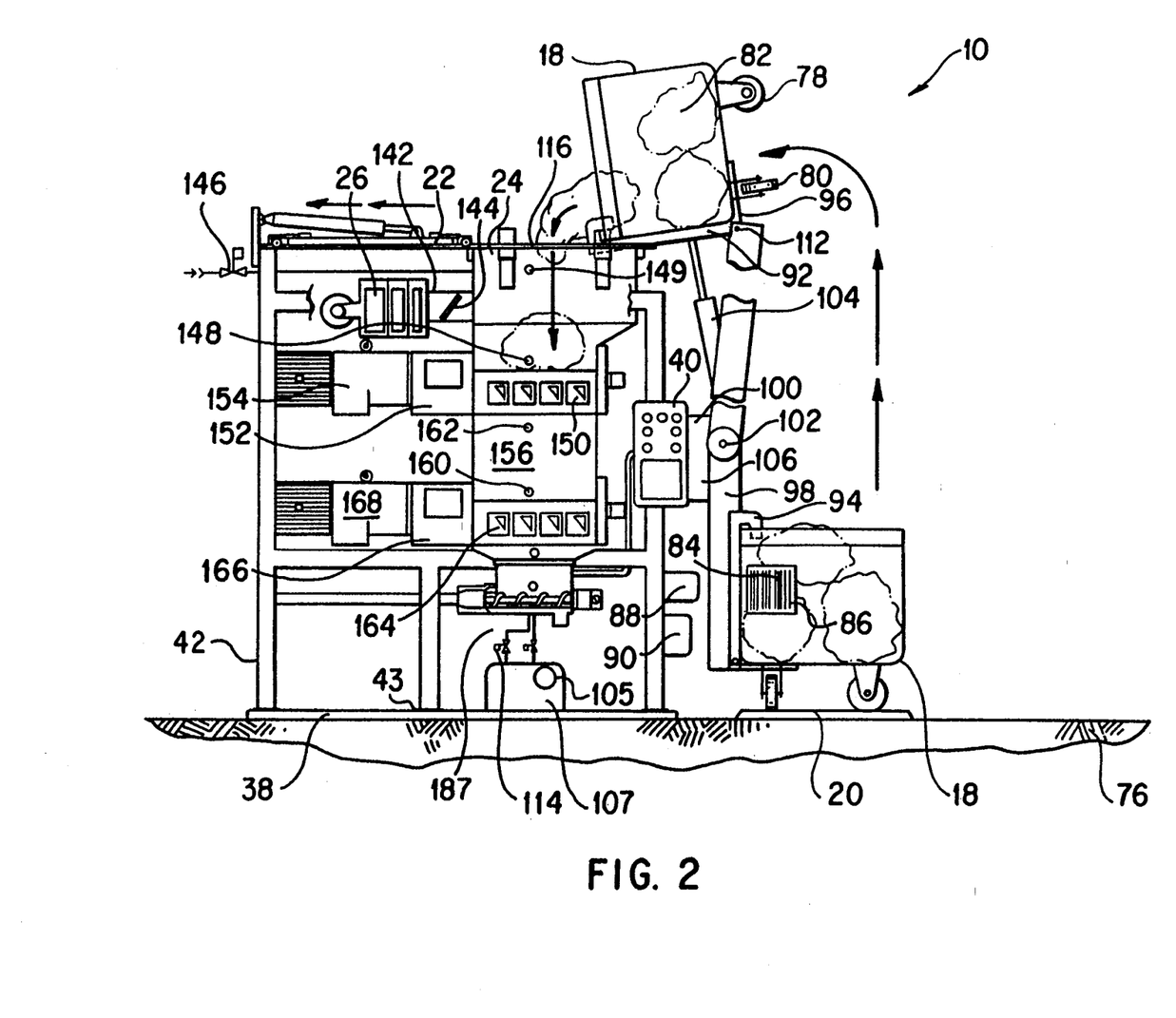
FIG. 2 is a front elevational view of the loader for loading of waste into the shredding system employed in the invention.

FIGS. 1 and 2 show an exemplary embodiment of an apparatus of the invention for shredding and neutralizing of biohazardous wastes such as medical wastes. The apparatus integrates automated container loader 16, container 18, shredding system 10, neutralization system 12, and process control system 14 to provide biohazardous waste processing facility 11.

Shredding system 10 includes sliding cover 22, loading chamber 24, multi-stage high-efficiency particulate air (HEPA) filtration and blower system 26, primary-stage shredder system 28, secondary-stage shredder system 30, structural support frame 42, transfer chamber 44, accumulation hopper 32, centrifugal blower 34, volumetric screw feeder 36, and discharge nozzle 188.

Figure 6:
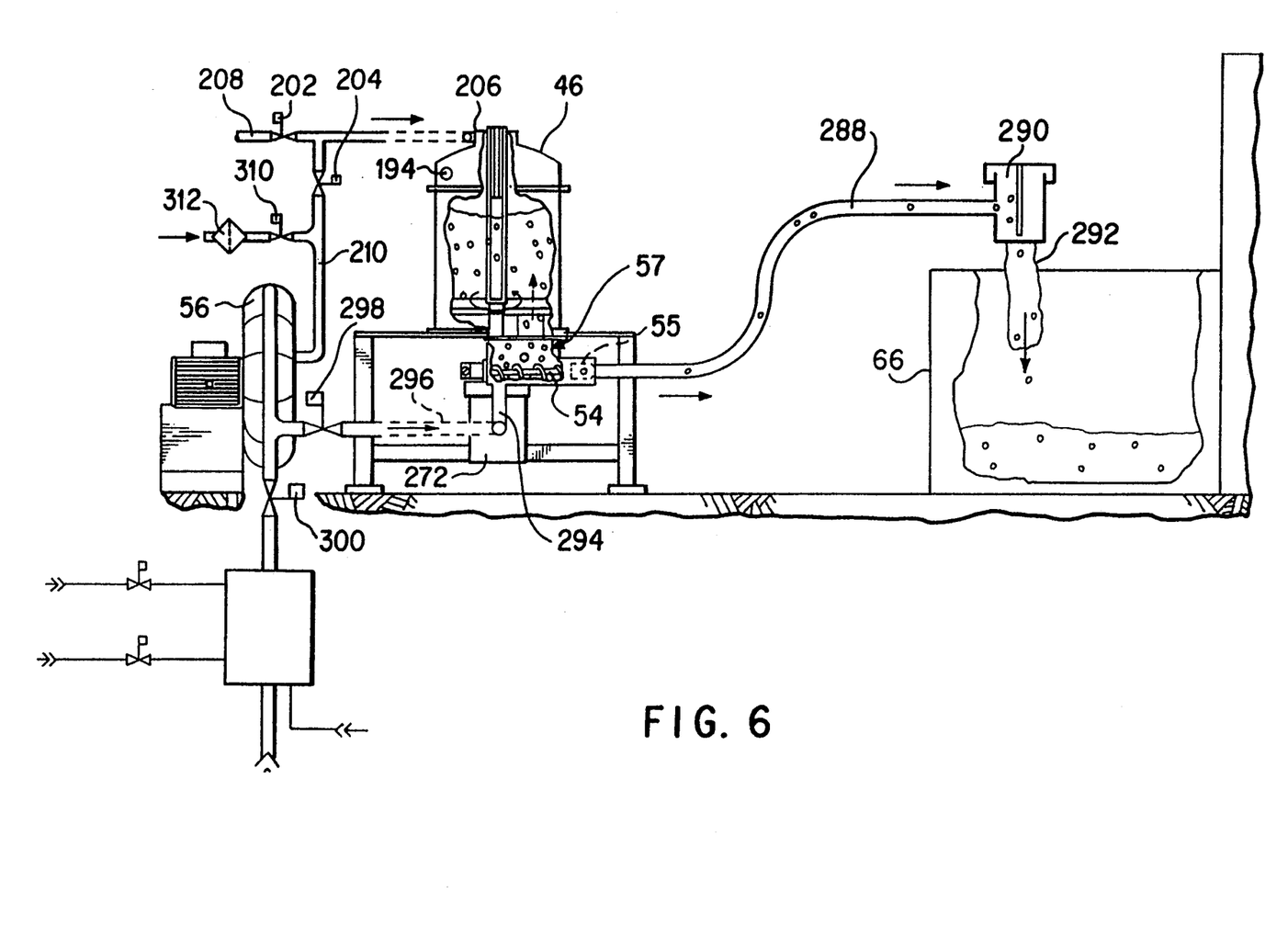
FIG. 6 is a side elevational view of the neutralization system of the invention.

Neutralization system 12, as shown in FIG. 1 and FIG. 6, incorporates cyclone cavity 46, radio-frequency heater applicator 48, neutralization chamber 49, RF generator 50, rotating pusher blade system 52, volumetric screw feeder 54, discharge nozzle 55, centrifugal blower 56, support table 58, structural support frame 60, steam condenser 64, industrial waste compactor 66, heater electrode 234, and discharge cyclonette 290.

Process control system 14 includes electrical control panel 68, graphical display monitor 70, microprocessor 72, and operator interface device 74, all of which are enclosed in housing 67. Control system 14 is electrically connected to receive freedback from weigh scales 20, 38 and 62, operater control panel 40, bar code scanner 88, low-level radiation detector 90, low-fill level sensors 148, 160, 176, high-fill level sensors 149, 162, 178, neutralization chamber filling level sensor 220, and temperature sensors 221.

As shown in FIGS. 1 and 2, container 18 is disposed on electronic weigh scale 20. Container 18 can be a mobile, industrial-grade, fluid-tight container of the type used by hospitals for temporary storage of medical waste 82. The body of container 18 can be constructed from a lightweight, durable, and chemical-resistant plastic such as polyethylene and can be strengthened with an exterior, tubular, steel frame (not shown) that encases the body of container 18. Container 18 can be equipped with front wheels 78 and rear swivel casters 80 to facilitate positioning of container 18 on weigh scale 20 for weight measurement and subsequent pickup by automated container loader 16. Removable cover 81 is attached to container 18 during periods of temporary storage of waste 82. Front wheels 78 and swivel casters 80 are preferably made of rubber such as neoprene.

Bar code label 84 bearing bar code 86 is affixed to the side wall of container 18 using any conventional pressure-sensitive adhesive. Bar code label 84 can be fabricated from thin matte anodized aluminum by methods known in the art. Bar code 86 is an alphanumeric sequence which uniquely identifies container 18 for tracking and validation of waste 82 by process control system 14. Bar code 86 is sealed in an anodized layer on label 84 to resist defacing, abrasion, and other harmful environmental conditions. Bar code 86 is photographically produced in black color onto bar code label 84 to provide good contrast for reading by bar code scanner 88 by methods known in the art. Bar code label 84 and bar code 86 are sufficient in size to provide for reading of bar code 86 by scanner 88 when container 18 is disposed on weigh scale 20 for pickup by container loader 16.

Container loader 16 is rigidly attached to support frame 42 by mounting frame 106. Frame 106 supports loader 16. Containers 18 can have different bar codes 86 for identifying, monitoring, and validating waste 82 which is processed in accordance with the invention.

Scanner 88 is mounted on support frame 42 so that bar code 86 can be read from the side of container 18. Attached to the lower part of support frame 42 is low-level radiation detector 90. Radiation detector 90 is oriented to scan waste 82 for the presence of low-level, radioactive material when container 18 is disposed on scale 20.

Container weigh scale 20 is of rectangular shape and is mounted on floor 76 adjacent to container loader 16. The length and width of weigh scale 20 are sufficient so that when container 18 is disposed on scale 20 that casters 80 of container 18 rest on and within scale 20.

FIG. 2 shows loader 16 in the pickup and dump positions. The pickup position is shown with container 18 resting on scale 20. The dump or unload position is shown with container 18 tipped or rotated counter-clockwise while in the elevated state. Loader 16 comprises rotatable attachment faceplate 92, adjustable stabilizer hook 94, lower support plate 96, rotary lift arm 98, hydraulic rotary actuator 100, revolute pivot joint 102, hydraulic cylinder 104, hydraulic pump 105, reservoir 107, and mounting frame 106. Faceplate 92, hook 94, plate 96, lift arm 98, and frame 106 are weldments constructed of cold-rolled steel. All components from mounting frame 106 to hook 94 form an articulated, mechanical linkage. Moving pivot joints 102 and 112 are equipped with self-lubricating bronze bushings and radial steel ball bearings or pillow block bearings. Frame 106 houses rotary actuator 100 and pivot joints 102. The fixed end of cylinder 104 is fastened to frame 106 and the extendible/retractable end is fastened to faceplate 92.

Hook 94 and lower support plate 96 are mounted to faceplate 92. Faceplate 92 is connected to lift arm 98 by pivot joint 112 which supports faceplate 92 both vertically and horizontally. Pivot joint 112 allows faceplate 92 to rotate freely about the end of lift arm 98. Cylinder 104 supports container 18 vertically in the dump position, and controls the tipping action of container 18 for dumping waste 82 into loading chamber 24. Lift arm 98 is connected to frame 106 by pivot joint 102. Actuator 100 provides torque at joint 102 for rotating faceplate 92 and lifting container 18 to the dump position as indicated in FIG. 2. Rotary actuator 100 is preferably based on a rack-and-pinion design. Pump 105 is the hydraulic power source for loader 16. Reservoir 107 holds hydraulic oil and supplies the oil to pump 105. Pump 105 delivers high-pressure oil to actuators 100 and 104. Process control system 14 and hydraulic control valves 114 provide smooth and jerk-free up/down motion of loader 16. Stop and reverse action is possible at any point in the cycle via semi-automatic control from operator control panel 40.

As shown in FIGS. 1 and 2, shredding system 10 includes slide cover 22, loading chamber 24, transfer chamber 44, accumulation hopper 32, and shredders 28, 30. Shredding system 10 is designed as an outwardly sealable pressure chamber. Loading chamber 24 is an enclosure with rectangular cross-section and is fabricated from steel sheet panels, preferably 11 gauge 304 stainless steel. All mating seams are welded fluid-tight and air-tight and are ground smooth. Loading chamber 24 has rectangular cutout opening 116 to permit dumping of waste 82 into shredding system 10. Loading chamber 24 is supported by structural support frame 42 disposed on base pads 43 which are seated on individual weigh scales 38. HEPA filter and blower system 26 is connected via duct 142 to loading chamber 24. HEPA filter and blower system 26 is preferably 99.7% efficient with a 3 micron pore size rating.

Mounted inside duct 142 is damper valve 144 for sealing loading chamber 24 from the atmosphere. Damper valve 144 is solenoid-actuated and pressure-loadable. Also attached to a side panel of loading chamber 24 is steam valve 146 which is connected to a steam service supply (not shown). Steam valve 146 is solenoid-actuated and pressure-loadable. Low-fill level sensor 148 and high-fill level sensor 149 are inserted into the front panel of loading chamber 24 for detecting the level of waste 82 in loading chamber 24. The bottom of loading chamber 24 is open-ended and is connected to the top inlet of primary-stage shredder 28.

Primary-stage shredder 28 comprises a portion of shredding system 10. Primary-shredder 28 comprises a cutting chamber that employs a plurality of hooked cutter wheels 150 attached to two counter-rotating shafts (not shown). The shafts rotate at different speeds to maximize the rate of ingestion and throughput of incoming biohazardous waste such as medical waste 82. The rotational speed of the shafts can vary from 10 to 70 revolutions per minute. Low rotational speeds prevent large objects from jamming the shredder and also enables shredder 28 to generate maximum torque using minimum energy. Cutter wheels 150 are intermeshed rotating knives fabricated from high-quality steel. Primary-stage shredder 28 is powered by motor 154 and transmission 152.

Figure 4:
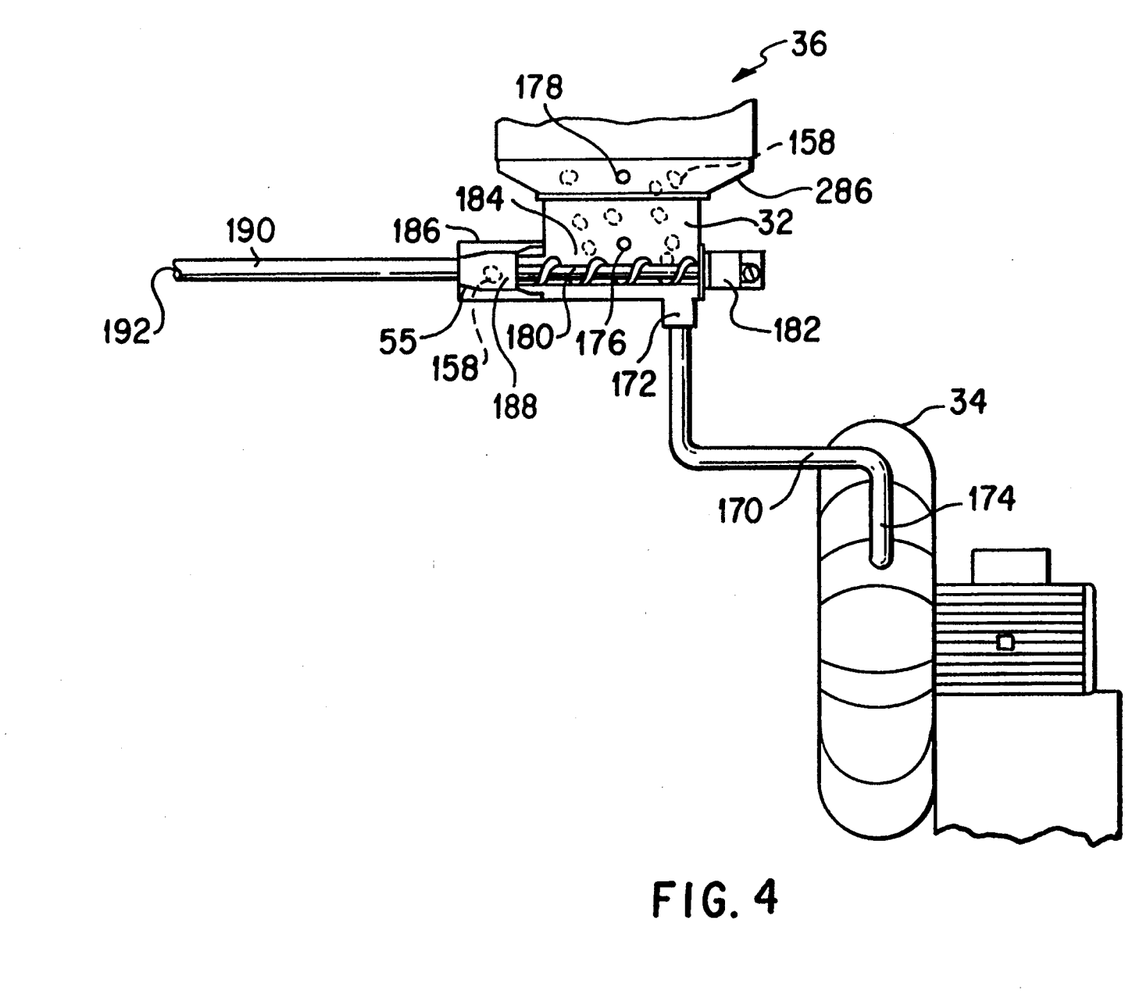
FIG. 4 is an assembly drawing of the volumetric screw feeder of the apparatus of the invention.

As waste 82 is drawn through shredder 28, it is shredded and discharged at the outlet of the shredder chamber into waste fragments which have a maximum size of about 1 inch. The waste fragments then pass through transfer chamber 44 and into secondary-stage shredder 30. As shown in FIG. 4, secondary-stage shredder 30 reduces the waste fragments into fully shredded waste particles 158 which measure about $\frac{1}{8}$ inch in their greatest dimension. Fully shredded waste 158 collects in feed hopper 184 inside accumulation hopper 32, also as shown in FIG. 4.

The shredding action provided by shredding system 10 is a destructive process by which incoming medical waste 82 is mechanically disintegrated. The shredding action provided by shredding system 10 effectively reduces the volume of incoming waste by about 80%. As a result, dissimilar and heterogeneous wastes such as paper, cloth, plastics, glass, metal, and fluids are transformed into a more homogeneous mixture with more uniform sizes, densities, specific heats etc. This allows for rapid and uniform heating of the waste by RF radiation as described below.

The outlet of primary-stage shredder 28 is connected to transfer chamber 44 and to the inlet of secondary-stage shredder 30. All adjoining connections are mated flush and all seams are air and fluid-tight. Transfer chamber 44 serves as a passageway for transferring partially fragmented 156 between primary-stage shredder 28 and secondary-stage shredder 30. Transfer chamber 44 is formed as an open-ended, rectangular enclosure and preferably is fabricated from 11 gauge 304 stainless steel. All mating seams are air and fluid-tight. Low-fill level sensor 160 and high-fill level sensor 162 are inserted into transfer chamber 44 for monitoring the level of waste fragments 156 in transfer chamber 44.

Secondary-stage shredder 30 is substantially identical in construction to primary-stage shredder 28. Secondary-stage shredder 30 is powered by motor 168 and transmission 166. Secondary-stage shredder 30 is equipped with hooked cutter wheels 164. Suitable secondary-stage shredders 30 are Model No. ST-20 from Shred-Tech International, Canada.

As shown in FIGS. 1 and 4, accumulation hopper 32 is connected to the bottom outlet of secondary-stage shredder 30. Accumulation hopper 32 serves as a temporary collection bin for shredded waste 158. Accumulation hopper 32 is a fluid-tight enclosure with rectangular cross-section, preferably fabricated from 11 gauge 304 stainless steel sheet. The top of accumulation hopper 32 is open-ended to receive shredded waste 158 passing through secondary-stage shredder 30. The bottom of accumulation hopper 32 is connected to pneumatic conveyor system 187.

Pneumatic conveyor system 187 employs volumetric screw feeder 36, discharge nozzle 188, centrifugal blower 34, transfer duct 190, waste inlet valve 192, waste inlet duct 196, air return valve 202, and air return duct 208. Volumetric screw feeder 36 is mounted in the lower section of accumulation hopper 32 so that screw feeder 36 is integral to accumulation hopper 32.

FIG. 4 shows the assembly of volumetric screw feeder 36. As shown, duct 170 connects bottom opening 172 of accumulation hopper 32 to outlet 174 of centrifugal blower 34. Low fill level sensor 176 and high-fill level sensor 178 are inserted into accumulation hopper 32 for monitoring the level of shredded waste 158. Volumetric screw feeder 36 comprises helix conveying screw or auger 180, gearmotor 182, feed hopper 184, and feed tube 186. Helix conveying screw 180, feed hopper 184, and feed tube 186 preferably are fabricated from 300 series stainless steel. The internal profile of feed hopper 184 ensures that all waste material collected within hopper 184 can be conveyed out by screw 180. A fluid-tight seal is maintained at the mating/adjoining connection between accumulation hopper 32 and feed hopper 184.

Gearmotor 182 is a parallel-shaft, permanent magnet gearmotor. Screw 180 is driven by gearmotor 182 for conveying and discharging shredded waste 158 through feed tube 186 and into discharge nozzle 188. Discharge nozzle 188 is attached to transfer duct 190 and the outlet of feed tube 186. Discharge nozzle 188 is a machined block of stainless steel which utilizes the venturi vacuum principle and the coanda effect to induce a high volume, high velocity flow of air from blower 34 to accelerate shredded waste 158 out of nozzle 188 and into transfer duct 190.

The outlet of transfer duct 190 is connected to waste inlet valve 192 on neutralization chamber 49, as shown in FIG. 1. Transfer duct 190 comprises hard-piped, stainless steel connections. Waste inlet valve 192 is a solenoid-actuated, pressure-loadable valve. All external steel surfaces of sliding cover 22, loading chamber 24, accumulation hopper 32, transfer chamber 44, and feed hopper 184 are covered with thermal insulation 286 to limit heat loss during periodic steam purging.

Figure 3A:
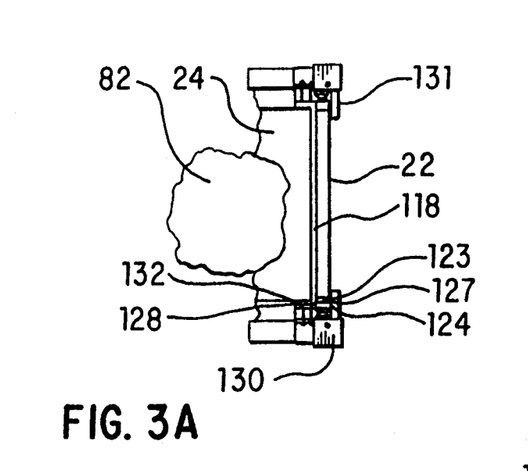
FIGS. 3A, 3B, and 3C show front, side, and top views of the sliding cover of the apparatus of the invention.
Figure 3B:
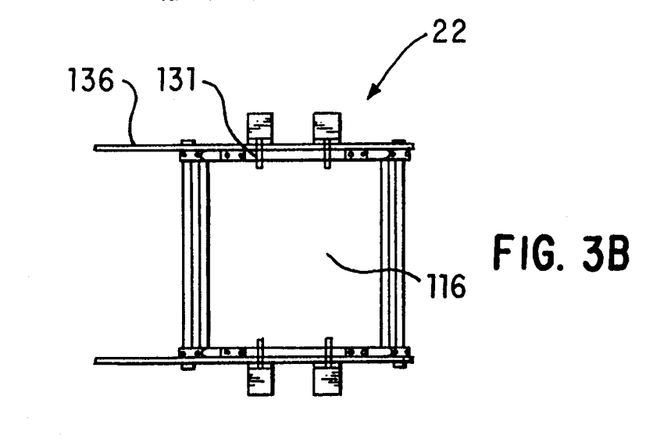
Figure 3C:
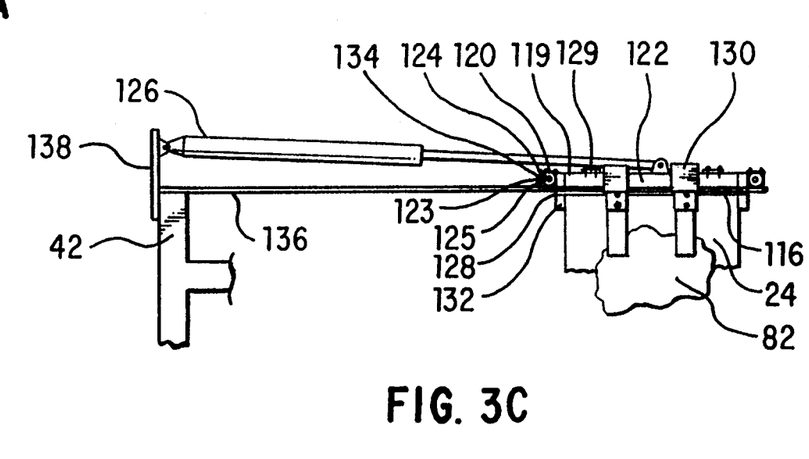

FIGS. 3A–3C show detailed assembly views of sliding cover 22. Sliding cover 22 include seal plate 118, leaf springs 119, track rollers 120, cover frame 122, bearing block 123, shaft axles 124, bushings 125, air cylinder 126, spacer plates 127, and hard pads 129. Plate 118 preferably is fabricated from 300 series stainless steel to resist corrosion from direct exposure to moisture. Plate 118 is flat and rectangular. The length and width of plate 118 are sufficient so that when cover 22 is in the fully closed and sealed position, opening 116 is completely covered by plate 118. In addition, the length and width of plate 118 are oversized to produce a minimum overlap of at least one inch around the entire perimeter of opening 116.

Plate 118 is sufficiently thick to accommodate the design pressure in loading chamber 24. Continuous gasket 128 is partially embedded within fixed bed 132 that surrounds opening 116 and, at the same time, is situated beneath the overlapping perimeter of plate 118 when plate 118 is in the fully closed position. Gasket 128 is a closed, seamless, flexible ring fabricated from a synthetic rubber such as perfluoroelastomer, teflon, fluorosilicone, or fluorocarbon which is resistant to high-temperature steam. Gasket 128 preferably has a quad-ring cross-section to ensure an air and fluid-tight seal when cover 22 is sealed. Fixed bed 132 is a weldment fabricated from 300 series stainless steel bar. Fixed bed 132 is a raised, rectangular framework which circumvents and abuts opening 116 and provides a seat for gasket 128. Leaf springs 119 are thin, elastic, flexible flat plates fabricated from tool steel, preferably oil-hardened tool steel to ensure good fatigue life and tensile strength.

Leaf springs 119 serve as flexible, cantilevered, suspension plates which connect shaft axles 124 to cover frame 122. Leaf springs 119 are bolted at one end to bearing block 123 and are bolted at the opposite end to cover frame 122. Hold-down clamps 130 are situated around the perimeter of opening 116, as shown in FIGS. 2 and 3A–3C, and are bolted to fixed bed 132. Hold-down clamps 130 are air-actuated devices. When clamps 130 are actuated, clamp beams 131 impact hard pads 129 and force plate 118 down into a seal position over opening 116, thereby partially crushing gasket 128 between plate 118 and fixed bed 132 resulting in sealing of loading chamber 24. Plate 118 is pushed down onto gasket 128 by virtue of leaf springs 119 which bend downward with plate 118 during sealing. The segment of leaf spring 119 which is rigidly attached to bearing block 123 is supported below by guide rail 136, preventing this segment from moving downward with plate 118 during sealing. The result is that leaf springs 119 are elastically stressed in the same manner as a loaded, cantilevered beam. When clamps 130 are released, leaf springs 119 return to their initial, unstressed state and thus return plate 118 to its initial, unsealed position above opening 116.

Cover frame 122 is a rectangular weldment fabricated from 300 series stainless steel. Cover frame 122 is mated and welded to the top face of plate 118 to increase the bending stiffness of plate 118. Two parallel, freely rotating shaft axles 124 are situated alongside cover frame 122 and are attached to cover frame 122 by leaf springs 119 bolted to bearing block 123. Spacer plates 127 stabilize and limit deflection of leaf springs 119 when cover 22 is pushed down into the seal position by hold-down clamps 130. Spacer plates 127 are sandwiched between pads 129 and leaf springs 119. Spacer plates 127 preferably are either carbon or stainless steel. Pads 129 are preferably made from tool steel to resist impact from clamp beams 131.

Rotating joints 134 are fitted with self-lubricating bronze bushings 125 which are press-fitted into bearing block 123. Track rollers 120 are rigidly pinned and keyed to the ends of shaft axles 124. Thus, track rollers 120 and shaft axles 124 rotate together as a single, rigid member. Track rollers 120 are seated on and supported by a pair of parallel and level guide rails 136 which span horizontally across the top of loading chamber 24 and structural support frame 42. Guide rails 136 are mounted to structural support frame 42.

Track rollers 120 of cover 22 roll freely along guide rails 136, enabling cover 22 to slide horizontally between the fully open and fully closed positions. Track rollers 120 preferably are fabricated from 300 series stainless steel and preferably have a 90 degree, inner V-groove cross-section which mates with guide rails 136. Guide rails 136 preferably are fabricated from 300 series stainless steel angle and are mounted in an inverted V-configuration to accept track rollers 120. Cover 22 is actuated by an air cylinder 126 which is mounted between plate 118 and support bracket 138. Support bracket 138 is rigidly fastened to frame 42.

Figures 5A, 5B, 5D:
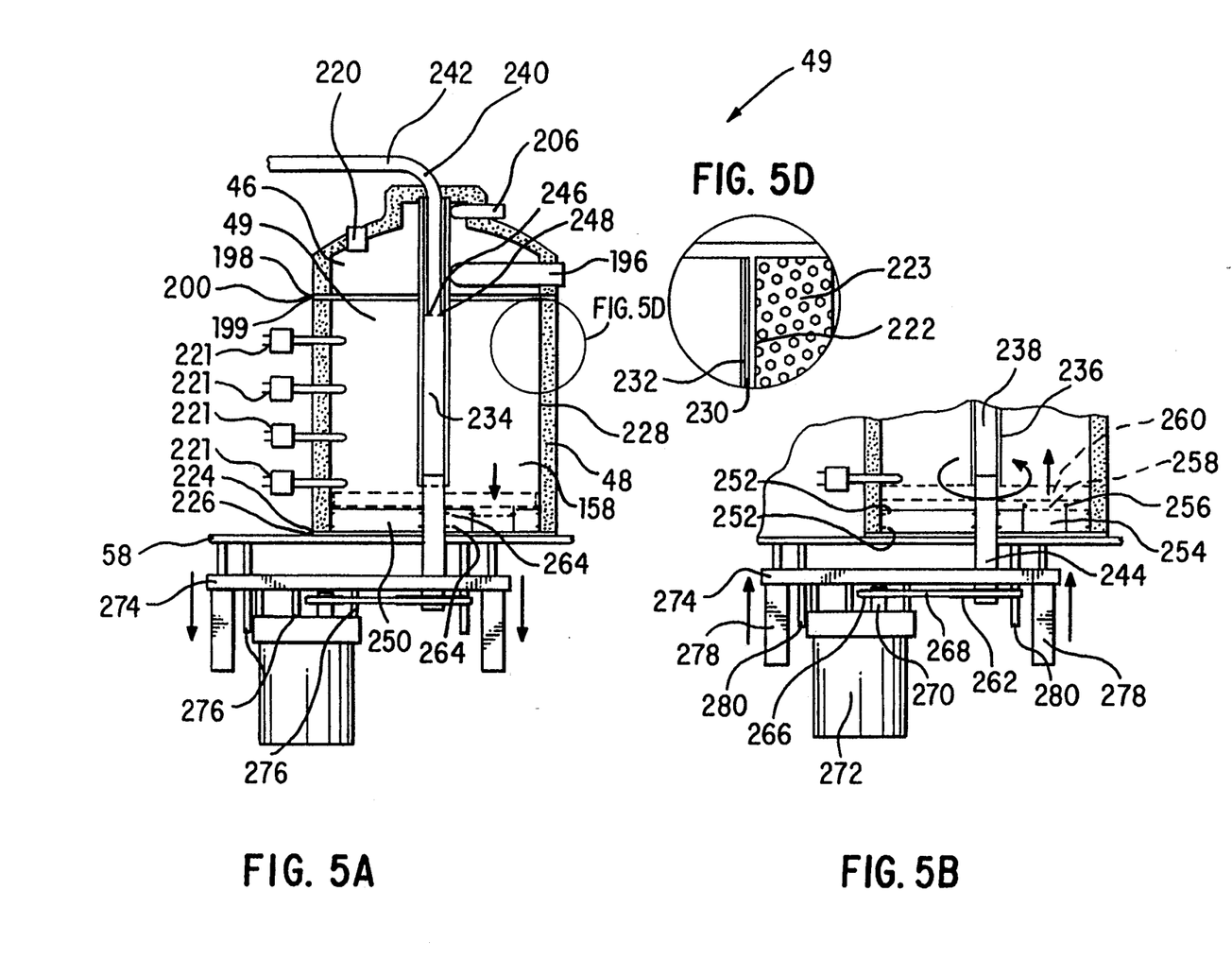
FIGS. 5A and 5B are front elevational views of the radio-frequency system employed in the invention.
FIG. 5D is a detailed enlargement of the radio-frequency heater side wall.

Neutralization chamber 49 is shown in FIGS. 1, 5A, and 5B. Cyclone cavity 46 and RF heater applicator 48 together form neutralization chamber 49. Neutralization chamber 49 is an outwardly sealable pressure vessel that can withstand an internal pressure of at least 15-20 psig. The outlet side of valve 192 is connected via waste inlet duct 196 to cyclone inlet opening 194 disposed on cyclone cavity 46. Inlet duct 196 preferably is fabricated from electrically non-conductive material.

Cyclone cavity 46 is disposed on RF heater applicator 48. Cyclone cavity 46 is a hollow structure with a parabolic or convex surface profile. Cyclone cavity 46 preferably is formed from 11 gauge 304 series stainless steel sheet. Upper sealing flange 198 is full-welded around the circumference of cyclone cavity 46. Sealing flanges 198 and 199 rigidly connect cyclone cavity 46 to RF heater applicator 48. Flanges 198 and 199 can be fabricated from 304 series stainless steel. Gasket 200 is disposed between sealing flanges 198. Gasket 200 is made from a synthetic rubber such as perfluoroelastomer, teflon, fluorosilicone, or fluorocarbon which is resistant to high-temperature steam.

The inlet sides of air return valves 202 and 204 are connected to cyclone outlet opening 206 located at the top of cyclone cavity 46. The outlet sides of air return valves 202 and 204 are connected to the inlets of blowers 34 and 56, respectively, via air return ducts 208 and 210, respectively. Air return valves 202 and 204 are solenoid-actuated, pressure-loadable valves. Steam feed valve 212 and compressed air feed valve 216 are connected to cyclone cavity 46. The inlet side of steam feed valve 212 is connected to steam service connection 214 from an external steam source such as a steam boiler (not shown). The inlet side of compressed air feed valve 216 is connected to compressed air service connection 218 from an external air source (not shown). Valves 212 and 216 are solenoid-actuated, pressure-loadable valves. Neutralization chamber filling level sensor 220 is inserted into cyclone cavity 46.

A plurality of temperature sensors 221 are inserted into neutralization chamber 49 through side wall 228. A minimum of four temperature sensors 221 are used to monitor the temperature of shredded waste 158 in neutralization chamber 49. Temperature sensors 221 are vertically situated along side wall 228 and are not necessarily equidistant from each other. The insertion depth of each sensor is substantially identical and is at least enough to fully penetrate the outer layer of shredded waste 158 when neutralization chamber 49 is fully loaded. Temperature sensors 221 are resistant to the harmful effects of continuous exposure to electromagnetic radiation and RF electric fields. Temperature sensors 221 are fiber optic temperature sensing micro probes which are part of a fiber optic temperature measurement system. The sensors are especially immune to high levels of electromagnetic interference (EMI), radio (RF), and microwave interference and are expressly chosen for this characteristic. Suitable sensors are Model T104-Fiber optic Micro Probe Assembly from MetriCor in Woodinville, Wash.

Figure 5C:
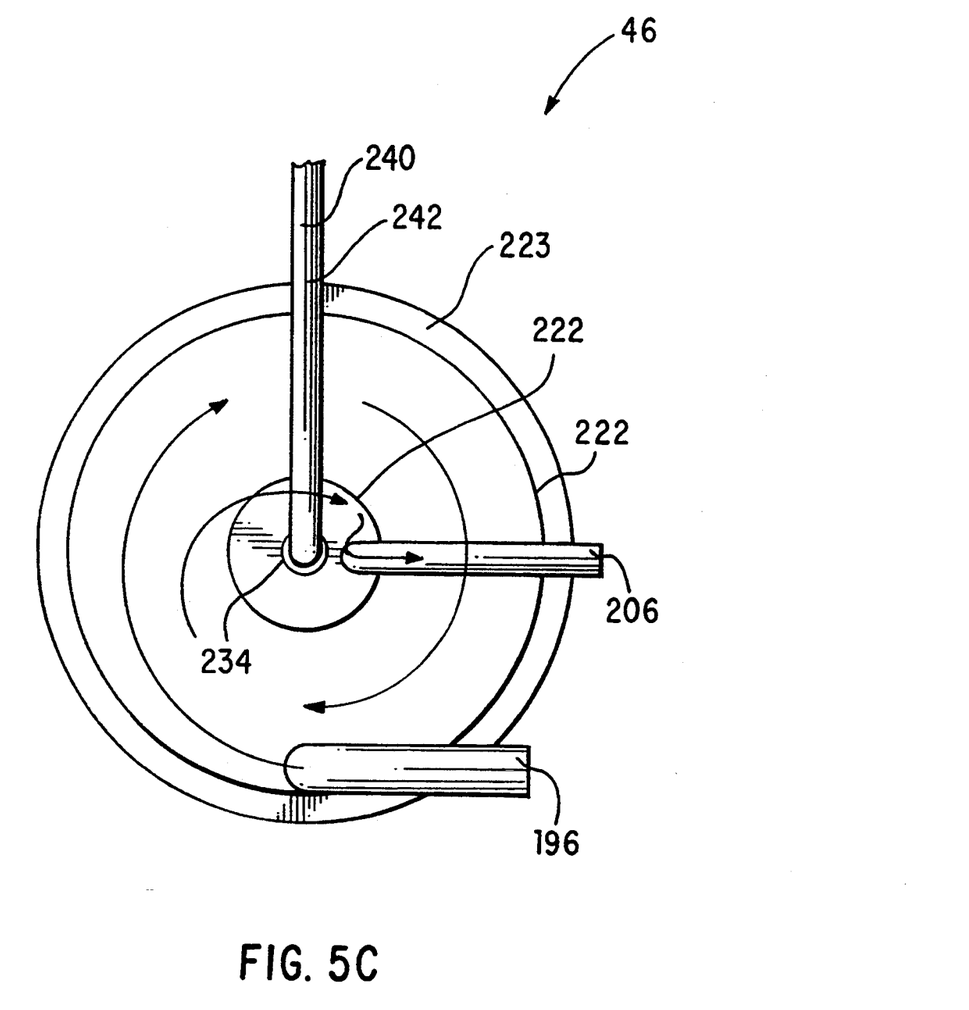
FIG. 5C shows a top view of the cyclone cavity which forms the upper half of the neutralization chamber of the apparatus of the invention. .

The detailed assembly of neutralization chamber 49 is shown in FIGS. 1, 5A, 5B, 5C and 5D. FIG. 5C shows a top view of cyclone cavity 46 which forms the upper half of neutralization chamber 49. The RF heater applicator 48, shown in FIG. 5A, forms the lower portion of neutralization chamber 49. Cyclone cavity 46 is constructed as an inverted, hollow, thin-walled, paraboloid structure. Heater applicator 48 is formed as a thin-walled hollow cylinder. The design and assembly of neutralization chamber 49 is such that the open-ended bottom of cyclone cavity 46 mates squarely with the open-ended top of heater applicator 48 via sealing flanges 198 and 199 to collectively form neutralization chamber 49.

The geometry of neutralization chamber 49 facilitates a uniform distribution of process parameters inside chamber 49 such as air pressure, shredded waste 158, supplied steam, thermal energy, and electromagnetic energy from the applied RF field.

The supporting structure of RF heater applicator 48 is a hollow, cylindrical, structural shell 222 fabricated from 304 series stainless steel sheet, preferably 11 gauge. All longitudinal weld seams of structural shell 222 are air and fluid-tight when subjected to internal pressure. Lower sealing flange 199 is welded around the circumference of structural shell 222. Flange base plate 224 is welded to the bottom end of structural shell 222 and is bolted to support table 58. Table 58 is mounted on structural support frame 60 which is disposed on weigh scale 62. Gasket 226 is disposed between flange base plate 224 and support table 58. Gasket 226 is made from a synthetic rubber which is resistant to high-temperature steam such as perfluoroelastomer, teflon, fluorosilicone, or fluorocarbon.

A detailed enlargement of side wall 228 is provided in FIG. 5D. Side wall 228 of RF heater applicator 48 comprises outer structural shell 222, ground electrode 230, and insulator shell 232. Ground electrode 230 is a thin-walled cylindrical tube. Ground electrode 230 is disposed on the inner surface of structural shell 222 by means of press-fit assembly. Ground electrode 230 is made from high electrical conductivity metal such as an alloy of aluminum, copper, gold, or silver. Ground electrode 230 can be supplied in the form of tubes or sheets.

Insulator shell 232 is disposed on the inner surface of ground electrode 230. Insulator shell 232 is made from a thin film material with high dielectric strength, stable electrical properties, high temperature resistance, broad chemical resistance, low moisture absorption, low dissipation/loss factor, low coefficient of thermal expansion, good abrasion resistance, good tensile and flexure strength. Preferred materials for insulator shell 232 include glass-filled or plain polyetherimide, hard glass, boro-silicate glass, polysulfone, polyester, polytetroflouroethylene (PTFE), or ultra high molecular weight polyethylene (UHMW). Insulator shell 232 is bonded to ground electrode 230 with adhesive. Preferred wall thickness of insulator shell 232 is 1/16th of an inch. The entire external surface of neutralization chamber 49 is covered with thermal insulation 223. Heater electrode 234 is suspended along the axial centerline of neutralization chamber 49 as shown in FIG. 5A.

Heater electrode 234 is a hollow cylindrical rod comprising outer insulator tube 236, inner conductor tube 238, power/coolant cable 240, and inlet and outlet coolant channels 242. The upper end of heater electrode 234 is rigidly attached to the top of cyclone cavity 46. The lower end of heater electrode 234 is stabilized by the upper end of blade shaft 244. The lower end of heater electrode 234 is counter-bored so that the upper end of blade shaft 244 loosely interlocks with the lower end of heater electrode 234. Insulator tube 236 can be made from the same dielectric material as insulator shell 232. The wall of insulator tube 236 is sufficiently thick to provide structural rigidity along the entire length of tube 236. The wall thickness of insulator tube 236 is uniform along the entire length.

Conductor tube 238 is fitted to the inner wall of insulator tube 236. Conductor tube 238 is concentric with insulator tube 236. Conductor tube 238 preferably is made from the same high-conductivity metal as ground electrode 230. Inlet and outlet coolant channels 242 are concentrically disposed inside the hollow center of heater electrode 234 for receiving of fluid. Power/coolant cable 240 connects conductor tube 238 to RF generator 50. Cable 240 feeds electromagnetic energy from RF generator 50 to heater electrode 234 for heating waste 158. Cable 240 also connects inlet and outlet coolant channels 242 to inlet coolant valve 246 and outlet coolant valve 248, respectively. Valves 246 and 248 are solenoid-actuated, pressure-loadable valves. Insulator disk 250 is disposed on flange base plate 224 at the bottom of neutralization chamber 49. The outer diameter of insulator disk 250 fits snugly against the inner diameter of neutralization chamber 49.

A pair of O-ring or quad-ring gaskets 252 are seated within the circumferential grooves of insulator disk 250. Gaskets 252 form a seal between the inner side wall of chamber 49 and insulator disk 250. Insulator disk 250 is a dielectric material such as glass-filled or plain polyetherimide, hard glass, boro-silicate, polysulfone, polyester, PTFE, or UHMW. Insulator disk 250 is sufficiently thick to prevent electromagnetic energy generated by heater electrode 234 from escaping through the bottom of neutralization chamber 49. Escapement hole 254 is located off-center within insulator disk 250. The centerline of escapement hole 254 is parallel to the axial centerline of neutralization chamber 49. An O-ring or quad-ring gasket 256 is seated within the side wall of escapement hole 254. In the sealed state, seal plug 258 of rotating pusher blade system 52 is inserted into escapement hole 254 as depicted in FIG. 5A.

As shown in FIG. 5B, seal plug 258 is integral to pusher blade 260 disposed above insulator disk 250. Pusher blade 260 is a rotating bar for pushing shredded waste 158 radially outward and downward through escapement hole 254. The radial profile of pusher blade 260 is adapted and configured for moving the waste in this manner.

Blade shaft 244 is rigidly fastened to the center of pusher blade 260. The upper end of blade shaft 244 engages the counter-bored end of insulator tube 236. The lower end of blade shaft 244 is rigidly fastened to both slide carriage 274 and to load sprocket 262. Slide carriage 274 fits onto blade shaft 244 by means of a hole in slide carriage 274. Blade shaft 244 is axially located through the centers of pusher blade 260 and insulator disk 250. The fit between blade shaft 244 and insulator disk 250 is a sliding clearance fit. Pusher blade 260 and blade shaft 244 rotate about the axial centerline of neutralization chamber 49.

A pair of rotary seal gaskets 264 are seated within the center bore of insulator disk 250. Gaskets 264 create a static and a dynamic seal between the inside of neutralization chamber 49 and the external atmosphere. Gaskets 252, 256, and 264 are fabricated from a synthetic rubber such as perfluoroelastomer, teflon, fluorosilicone, or fluorocarbon which is resistant to high-temperature steam. Pusher blade 260 and blade shaft 244 are fabricated from glass-filled or plain polyetherimide, hard glass, boro-silicate, polysulfone, polyester, PTFE, or of other compatible UHMW product. Pusher blade 260 and blade shaft 244 are driven by a chain-sprocket transmission and gearmotor assembly located beneath support table 58. Load sprocket 262 is mechanically linked to drive sprocket 266 by means of roller chain 268. Drive sprocket 266 is fastened to motor shaft 270.

Gearmotor 272 drives pusher blade 260 by means of a mechanical transmission comprising load sprocket 262, drive sprocket 266, and roller chain 268. Gearmotor 272 is preferably a parallel-shaft, permanent magnet gearmotor. Gearmotor 272 is mounted to slide carriage 274 with standoff rods 276. Slide carriage 274 travels vertically along parallel guide rods 280 by means of two pneumatic cylinders 278, enabling slide carriage 274 to travel up and down. Guide rods 280 are rigidly mounted to support table 58. Pneumatic cylinders 278 are mounted between stationary support table 58 and slide carriage 274. When both of cylinders 278 are actuated, slide carriage 274 is pulled up. When both of cylinders 278 are deactivated, slide carriage 274 moves down by gravity. Thus, rotating pusher blade system 52, comprising pusher blade 260, blade shaft 244, seal plug 258, load sprocket 262, drive sprocket 266, roller chain 268, slide carriage 274, gearmotor 272, and pneumatic cylinder 278, is a single, rigid assembly which slides vertically to an up position and to a down position. The significance of the vertical motion of slide carriage 274 is evident when carriage 274 is in either the up or the down position. When carriage 274 is in the down position, as depicted in FIG. 5A, seal plug 258 is fully inserted into escapement hole 254 to thereby effectively seal off the bottom of neutralization chamber 49. Thus, the down position of system 52 is the sealed position. Conversely, as shown in FIG. 5B, the up position of system 52 is the unsealed position. Pusher blade 260 can only rotate when system 52 is in the up/unsealed position so that seal plug 250 is completely removed from escapement hole 254.

FIGS. 5A, 5B, and 6 show elevation views of neutralization system 12. A second pneumatic conveyor system 57, comprising volumetric screw feeder 54, discharge nozzle 55, centrifugal blower 56, discharge duct 288, air return valve 204, air return duct 210, transfer duct 296, and blower outlet valve 298 for conveying waste out of chamber 49 is mounted directly beneath neutralization chamber 49. The internal construction of volumetric screw feeder 54 is identical to the construction of volumetric screw feeder 36. Volumetric screw feeder 54 and discharge nozzle 55 are connected to escapement hole 254. The outlet of nozzle 55 is connected to discharge duct 288 which feeds into discharge cyclonette 290. Deflector bag 292, suspended inside waste compactor 66, is attached to the outlet of discharge cyclonette 290. Blower air inlet valve 310 is connected in parallel with valve 204 off of air return duct 210. The inlet side of valve 310 is left open to atmosphere and is fitted with air inlet filter 312. The outlet of centrifugal transfer blower 56 is connected to the bottom opening 294 of screw feeder 54 by transfer duct 296. Blower outlet valve 298 is connected within transfer duct 296. As shown in FIGS. 1 and 6, condenser inlet valve 300 is connected in parallel with valve 298 to the outlet of blower 56. Valve 300 evacuates air and steam from inside neutralization chamber 49 into steam condenser 64. Cold water inlet valve 302 and cold water outlet valve 304 are connected to condenser 64. Condenser 64 discharges neutralized waste water 306 and neutralized air 308. Valves 298, 300, 302, 304, and 310 are electric, solenoid-actuated valves and are pressure-loadable.

To provide input to the apparatus of the invention, as shown in FIGS. 1 and 2, container 18 which contains biohazardous waste, such as medical waste 82, is positioned on electronic weigh scale 20. The weight of container 18 is recorded in an electronic database file (not shown). This database file is created and stored by process control system 14 by methods known in the art when container 18 is introduced to waste processing facility 11. Each container 18 therefore has a unique database file to provide verification of disposal of waste 82.

As shown in FIG. 2, automated container loader 16 is in the pickup position for engaging container 18. Container 18 then is attached to container loader 16 by engaging plate 96, stabilizer hook 94, and adjustable faceplate 92. This ensures that cover 81 is removed from container 18 before container 18 is lifted by loader 16. Preferably, after container 18 is attached to loader 16, bar code scanner 88 reads bar code 86 or bar code label 84. Optionally, label 84 can be scanned with a hand-held device (not shown). The bar-coded information is stored in the aforementioned electronic database file. At the same time, detector 90 scans the contents of container 18 to identify radioactive material. If radioactivity is detected in container 18, an alarm message is presented on graphical display monitor 70 and the loading process can be terminated. Monitor 70 can also display other possible alarm conditions so that operators can be alerted to possible malfunctions of the process. All alarm conditions and system malfunctions can automatically be logged into an alarm database file (not shown) created by process control system 14 by methods known in the art. In this way, a chronological history of all alarm conditions can be accessed and used in a validation protocol.

If no alarm conditions are generated, container 18 is ready to be lifted by loader 16. At this stage, control system 14 automatically performs the following actions before activating loader 16: internally seals off shredding system 10; activates primary-shredder 28 and secondary-shredder 30; activates (HEPA) filter and blower system 26; and unseals and opens sliding cover 22. Control system 14 preferably performs these actions in sequence to prevent escape of waste from shredding system 10.

HEPA filter and blower system 26 function to prevent escape of contaminates by producing a "negative" pressure within chamber 24. This "negative" pressure produces a flow of air from the outside atmosphere, preventing possibly contaminated air from flowing out of chamber 24. HEPA filter 26 has pores of 3 microns and an efficiency of 99.7% in preventing bacteria from escaping to the outside atmosphere. This method of generating "negative" pressure using a HEPA filtration system is a known technique for containing contaminates such as radioactive particles.

As shown in FIG. 2, sliding cover 22 is in the fully open position and loading chamber 24 is prepared to receive medical waste 82 from container 18. As shown in FIG. 2, loader 16 lifts container 18 to the dump position and empties medical waste 82 into loading chamber 24 and primary-stage shredder 28. After dumping waste 82, loader 16 returns to the pickup position for loading of the next container 18. Cover 22 closes and seals loading chamber 24. After cover 22 is sealed, HEPA filter and blower system 26 is deactivated and damper valve 144 is closed to seal shredding system 10 from the outside environment. Alternatively, high pressure steam from steam purge valve 146 can be injected to neutralize shredding system 10 as part of a separate purging operation. Such a purging operation may be necessary as part of a routine procedure for machine shutdown or maintenance and repair.

Waste processing facility 11 provides either continuous or batch processing of medical waste 82 even though the shredding, conveying, and neutralization processes are intermittent. Process control system 14 continuously monitors and controls the rate of throughput of neutralized waste from facility 11 by monitoring the fill levels, the running times of shredding system 10, and neutralization chamber 49. Fill levels are measured by high and low-fill level sensors 148, 149, 160, 162, 176, 178 in shredding system 10 and by filling level sensor 220 in neutralization chamber 49. These sensors provide inputs to control system 14 for controlling the filling levels of shredding system 10 and neutralization chamber 49. Such fill level sensors are known in the art. The control action provided by system 14 includes varying and alternating the running times of loader 16, shredders 28, 30, pneumatic conveyor system 187, and neutralization chamber 49 to maximize the rate of throughput of neutralized waste.

As shown in FIGS. 2 and 4, pneumatic conveyor system 187 for transporting shredded waste 158 from feed hopper 184 to neutralization chamber 49 is provided. System 187 includes volumetric screw feeder 36, discharge nozzle 188, centrifugal blower 34, transfer duct 190, waste inlet valve 192, waste inlet duct 196, air return valve 202, and air return duct 208.

Pneumatic conveyor system 187 functions as a closed and contained system. The air used to transport shredded waste 158 is recirculated within the system and thus no contaminated air emissions are produced. Shredding system 10, pneumatic conveyor system 187, and neutralization chamber 49 thereby collectively function as a closed and contained system during shredding, transporting, and heating of waste 158.

Pneumatic conveyor system 187 operates in the following manner. Volumetric screw feeder 36 pushes shredded waste 158 out of feed hopper 184 by rotating conveying screw 189. Upon exiting feed hopper 184, shredded waste 158 enters discharge nozzle 188 and is accelerated by high velocity flow of air through transfer duct 199 into cyclone inlet opening 194 caused by the "negative" pressure gradient created by nozzle 188 and blower 34. By virtue of the design of cyclone cavity 46, shredded waste 158 enters cyclone cavity 46 and is separated from the high velocity air and falls to the bottom of neutralization chamber 49. The high velocity air, in turn, exits through cyclone outlet opening 296 and returns to the inlet side of blower 34 through air return duct 298. Thus, pneumatic conveyor system 187 is a closed-loop process.

Cyclone cavity 46 separates shredded waste from the high velocity air stream which enters cyclone cavity 46 generated from pneumatic conveyor system 187. As the high velocity air stream enters cyclone cavity 46 through waste inlet duct 196, shredded waste 158 impinges and rubs against the inner wall of cyclone cavity 46. By virtue of the circular contour of cyclone cavity 46, waste 158 is forced to centrifugally spin in a circular path against the inner wall of cyclone cavity 46 to rapidly decelerate waste 158 and to fall out of cyclone cavity 46 into neutralization chamber 49. In addition, as shredded waste 158 is separated from the influx of air and waste material, the remaining air exits cyclone cavity 46 through outlet opening 206 as depicted in FIG. 5C. This air is then recirculated back to blower 34 for reuse by pneumatic conveyor system 187 for transporting additional shredded waste 158 into neutralization chamber 49.

Next, as shown in FIGS. 1 and 5A, shredded waste 158 is transferred from shredding system 10 into neutralization system 49 for heating by electromagnetic (EM) waves. Radiofrequency (RF) waves, as is known in the art, can be generated between a conductor electrode and a ground electrode. The conductor electrode converts RF electricity into RF waves. The frequency range of the EM waves useful in the invention can vary from about 10 kilohertz (KHz) to 300 gigahertz (GHz). For RF heating, useful frequencies are generally between 1–200 megahertz (MHz). RF waves can be employed to heat a variety of materials, including dielectrics.

Heating with RF waves in accordance with the invention has several surprising advantages. A particular advantage is that the RF source which supplies the energy can be switched on and off quickly to control the rate of heating and the temperature of the heated material. High frequencies (above 100 megahertz) promote more rapid heating but have shorter penetration. Conversely, low frequencies (below 100 megahertz) produce slower, more uniform heating and penetrate deeper into densely-packed materials. Another advantage is that RF heating can be precisely and accurately controlled with simple devices. Additionally, RF heating equipment is straightforward to operate, is robust, and requires little maintenance.

As mentioned, shredded waste 158 is removed from feed hopper 184 and placed into neutralization chamber 49 by pneumatic conveyor system 187 such as in a batchwise manner. As shown in FIG. 5A, neutralization chamber 49 comprises cyclone cavity 46, RF heater applicator 48, insulator disk 250, and rotating pusher blade system 52. During shredding, loading, and heating of shredded waste 158, neutralization chamber 49 is sealed from the outside atmosphere. This prevents shredded waste 158 and contaminated air from escaping from neutralization chamber 49. To seal neutralization chamber 49, pusher blade 260 is maintained in the down/sealed position by cylinders 278 so that seal plug 258 is inside escapement hole 254.

As shown in FIG. 5A, shredded waste 158 accumulates on top of insulator disk 250 located at the bottom of neutralization chamber 49. Filling level sensor 220 monitors the fill level of waste 158 in neutralization chamber 49. When sensor 220 detects that the maximum fill level in chamber 49 is reached, pneumatic conveyor system 187 stops to discontinue loading of waste 158. The result is that heater electrode 234, located in the center of neutralization chamber 49, is embedded within the shredded waste 150.

RF heater applicator 48 includes structural shell 222, ground electrode 230, heater electrode 234, and cable 240. Ground electrode 230 is a thin, metallic shell built into side wall 228 of shell 222. Heater electrode 234 includes a conductor tube or rod 238 which is connected to RF generator 50 via cable 240. When electrode system 230, 234 is supplied with continuous radio frequency power from RF generator 50, RF waves are created within neutralization chamber 49 which rapidly heat shredded waste 158 in neutralization chamber 49. Also, as shredded waste 158 is heated by RF radiation, neutralization chamber 49 is pressurized with compressed air provided through air feed valve 216. Preferably, the working pressure inside neutralization chamber 49 is about 15 to about 21 pounds per square inch gauge (psig). More preferably, the internal working pressure is in the range of about 15 to about 18 psig most preferably, about 16.5 psig. Also, all inlet and outlet connections of the neutralization chamber 49 are sealed in an air and fluid-tight manner by means of valves 202, 204, 192 and seal plug 258. In this way, neutralization chamber 49 is outwardly sealed and pressure-loadable. The pressure in chamber 49 automatically can be adjusted by compressed air from air feed valve 216. Addition of compressed air intensifies and speeds up the rate of heating of the shredded waste 158 in neutralization chamber 49. Moreover, by pressurizing chamber 49, shredded waste 158 is compacted to further reduce the volume of waste 158 and increase the rate and the uniformity of heating.

After chamber 49 is pressurized, high temperature, high pressure steam is injected into neutralization chamber 49. The amount of steam injected into chamber 49 is controlled by steam feed valve 212. Preferably, the temperature of the steam is 132° C. to 171° C. At least four temperature sensors 221 in chamber 49 are used to monitor the temperature of the waste heated by the steam. Preferably, the final temperature of shredded waste 158 in neutralization chamber 49 is about 100° C.–124° C., more preferably, 118° C.–124° C., most preferably, 121° C. Preferably, the desired temperature in the waste is over 100° C., preferably 120° C.–124° C. The temperature can be regulated by feedback from temperature sensors 221 and control system 14.

Temperature regulation of the waste in chamber 49 can be achieved any of either of the following methods: 1) adjusting the temperature of the supply steam; 2) adjusting the pressure of the compressed air supply; 3) adjusting the frequency of the RF waves applied to the waste; 4) adjusting the power density of the RF field in chamber 49 by changing the voltage applied to RF generator 50; or 5) intermittent pulsing of the heater electrode 234. Methods 1, 3, 4, and 5 are more preferable. Methods 1 and 5 are most preferable. The specific pressures and temperatures can readily be determined by the art skilled for specific amounts and types of waste.

The advantage of injecting steam into chamber 49 is that the steam directly heats the waste by virtue of its high temperature and good penetrability. Initially, since the waste is relatively cool, the steam condenses into water as it penetrates to heat the waste internally. The condensed water absorbs RF radiation and heats up quickly to increase the rate of heating of the waste. Heating of the condensed water also destroys any viruses which may be in shredded waste 158.

An advantage of pressurizing neutralization chamber 49 to about supernatant pressures such as 16.5 psig is that a high neutralization temperature can be achieved rapidly, uniformly, and efficiently by preventing the formation of excess steam inside chamber 49. Since the amount of energy required to convert liquid water to saturated steam is large, more RF energy is available for directly heating waste 158. Thus, no RF energy is wasted in creating additional saturated steam, and no RF energy is used to convert condensed water into saturated steam.

After shredded waste 158 reaches a desired final temperature, as indicated by temperature sensors 221, waste 158 is maintained at that temperature for sufficient time to ensure neutralization of the waste 158. During this time, process control system 14 continuously records the temperature profile history along with other relevant physical parameters inside the neutralization chamber 49 such as pressure, steam temperature, relatively humidity, weight of the waste etc. This data is used by the control system 14 to validate the neutralization process. Then, the neutralized waste is discharged through escapement hole 254 at the bottom of neutralization chamber 49.

Discharging of neutralized waste is shown in FIGS. 1 and 6. The first stage of the discharge process is rapid evacuation of moist air and moisture trapped in the neutralized waste. Rapid evacuation is achieved by unsealing seal plug 254 and activating centrifugal blower 56. Blower 56 produces a "negative" pressure and high flow of air to cause rapid evaporation of moisture in the solid waste as moist air is pulled out of neutralization chamber 49. The moist air travels out of the top of cyclone cavity 46 through air return duct 210, through housing (not shown) of blower 56, through blower outlet valve 298, and into steam condenser 64. Steam condenser 64 removes moisture from the air and discharges neutralized water and neutralized air so that neutralization chamber 49 and the resulting neutralized solid waste are dry. The dried solid waste is removed from chamber 49 by pneumatic conveyor system 57 and placed into compactor 66.

In the final stage of the discharge process, as shown in FIGS. 59 and 6, seal plug 254 remains unsealed with rotating pusher blade 260 in the fully up position. Pusher blade 260 slowly rotates to loosen and push the waste radially toward and through escapement hole 254. At the bottom of escapement hole 254, the neutralized waste empties into feed hopper 284 of volumetric screw feeder device 54 which, in turn, pushes the neutralized waste into discharge nozzle 55. Discharge nozzle 55, in conjunction with blower 56, accelerates and conveys the neutralized waste through discharge duct 288 and into discharge cyclonette 290. Finally, the neutralized waste decelerates in cyclonette 290, falls through deflector bag 292, and discharges directly into compactor 66 where they are compacted before final disposal by transportation.

During discharge of neutralized waste, pneumatic conveyor system 57 operates as an open-loop system since the air blower inlet valve 310 and discharge duct 288 are connected to the outside atmosphere. However, the air emissions from discharge duct 288 are contamination-free since the inlet air 312 from the outside atmosphere is both pre-filtered and kept isolated and closed off from the contaminated section of shredding system 10 by means of sealable valves 192 and 202. The discharging process continues until virtually all of the neutralized waste is emptied from the neutralization chamber 49. Then, the next charge of shredded waste is loaded into the neutralization chamber 49 and processed in the same manner as described above.

A validation procedure can be provided to ensure that infectious and potentially infectious microorganisms are effectively and consistently destroyed by the neutralization process described in the present invention. In this way, the apparatus can be continuously evaluated to maintain the system in a validated state. Prior to implementing the proposed validation procedure, written approval from regulatory agencies may be necessary.

As part of the present invention, a useful validation procedure can be based on setting of specific operating parameters of the facility 11 which consistently destroy *Bacillus stearothermophilus* spores contained in a test sample. *Bacillus stearothermophilus* spores are chosen because the spores of the bacteria are particularly resistant to heat. The test sample will contain live *Bacillus stearothermophilus* spores with a known population count. The test sample is sealed in a container which is translucent to electromagnetic radiation so that the bacterial spores will be exposed directly to the RF field in neutralization chamber 49. The test sample is inserted directly into neutralization chamber 49 via a connection on waste inlet duct 196 of cyclone cavity 46.

In performing a validation, neutralization chamber 49 will contain a typical load of shredded waste 158 (non-infectious) to simulate as accurately as possible the actual operating load conditions of neutralization chamber 49. The test sample and shredded waste 158 are then subjected to a complete neutralization cycle. Process control system 14, including all of the sensors and controls, monitors and records the time history of all measured process variables of a given validation analysis. The final settings of physical variables such as steam temperature, air pressure, RF field strength, and cycle time for disinfection or sterilization, can be based on prior analysis and feedback from previous trial-and-error validation runs.

After the neutralization cycle is complete and waste 158 is purged from chamber 49, the test sample is retrieved from the waste stream. The population count of the test sample is determined by methods known in the art and, if applicable, the decline of the population count of the bacteria can be expressed as a log reduction. If the log reduction is sufficient to conclude that neutralization of the test sample is achieved, the validation procedure can be repeated at the same settings of the process variables to ensure consistent neutralization of the test sample. Assuming consistent neutralization, the settings of the process variables can be stored as a permanent, non-volatile part of the process control software for running biohazardous waste processing facility 11.

Sterilization of biohazardous waste can be verified by assuring that the process variables are controlled and maintained at their minimum validated settings for the entire duration of the process cycle. The time history of the process variables can be automatically data-logged into a computer file which is specific for each batch of waste 158 processed in neutralization chamber 49. A hard copy verification report can be provided for each batch of waste 158. Periodically, the validation procedure can be repeated in order to maintain facility 11 in a validated state.

The foregoing description of the invention has been presented for the purposes of illustration and description. Many other modifications and variations are possible with respect to the above descriptions. For example, the automated container loader 16 can be easily replaced by any other manual or automatic loading processes which can effectively place the waste into loading chamber 24. In addition, neutralization system 12 can operate as an independent unit without shredding system 10 as long as means are provided for loading shredded waste into neutralization chamber 49 in a safe manner. Furthermore, the physical size of the neutralization chamber 49 need not be fixed but rather may include means of varying its dimensions, in particular its diameter in this case, to achieve, for example, different capacities and regulation of the temperature of the waste.

We claim:

1. A method for neutralizing biohazardous waste comprising subjecting said waste to steam while maintaining said waste under superatmospheric pressure to generate water in said waste, and maintaining said pressure while subjecting said waste having said water therein to electromagnetic radiation to generate water at a temperature of about 132°–171° C. and pressure of about 15–18 psig to neutralize said waste.

2. The method of claim 1 in which said pressure is about 16.5 psig.

3. The method of claim 1 wherein said steam has a temperature of about 132° C.–171° C.

4. The method of claim 3 wherein said waste is medical waste.

5. The method of claim 4 wherein said electromagnetic (EM) radiation has a frequency of about 10 KHz–300 GHz.

6. The method of claim 4 wherein said electromagnetic radiation is RF radiation that has a frequency of about 1–200 MHz.

7. The method of claim 1 wherein said water is generated in the absence of steam.

8. An apparatus for neutralizing biohazardous waste comprising, in combination, means for introducing biohazardous waste into a neutralization chamber to provide said waste in said chamber, means for producing super atmospheric pressure in said chamber, means for providing steam to said chamber in the presence of superatmospheric pressure in said chamber to generate water in biohazardous waste present in said chamber, and means for subjecting biohazardous waste present in said neutralization chamber to electromagnetic radiation in the presence of super atmospheric pressure in said chamber, whereby interaction of said radiation with water present in said biohazardous waste while in the presence of super atmospheric pressure in said neutralization chamber generates water of temperature of about 132°–171° C. and pressure of about 15–18 psig to neutralize said waste.

9. The apparatus of claim 8 wherein said means for introducing said waste into said chamber comprises means for shredding said waste, and means for transporting said shredded waste into said chamber.

10. The apparatus of claim 9 wherein said chamber, and said means for introducing said shredded waste into said chamber are in fluid tight connection.

11. The apparatus of claim 8 further comprising means to detect radioactive material in said biohazardous waste.

12. The apparatus of claim 11 wherein said biohazardous waste in medical waste.

13. The apparatus of claim 12 wherein said apparatus further comprises means for preventing fluid and solid containments in said shredded waste from escaping said apparatus.

14. The apparatus of claim 13 wherein said means for preventing said contaminates from escaping said apparatus includes means to generate negative atmospheric pressure in at least a loading chamber.

15. The apparatus of claim 14 wherein said apparatus further includes means for sensing temperature of said waste in said chamber.

16. The apparatus of claim 15 wherein said means for shredding of said biohazardous waste achieves 80% volume reduction of said materials.

17. An apparatus for neutralizing biohazardous waste comprising, a loading chamber having a sealable cover for receiving biohazardous waste, at least one shredder for shredding biohazardous waste to provide shredded waste, a conveyor to transport the shredded waste into a neutralization chamber, a radio-frequency heater applicator for generating radio-frequency radiation in said chamber to treat waste in said chamber to said radiation, means for introducing pressurized air into said neutralization chamber to achieve super atmospheric pressure in said chamber, means for introducing steam into said neutralization chamber when super atmospheric pressure is present in said chamber to generate water in biohazardous waste in said chamber whereby interaction of said radiation with water in biohazardous waste in said neutralization chamber while superatmospheric pressure is present in said neutralization chamber generates water of temperature of about 132°–171° C. and pressure of about 15–18 psig to neutralize said waste.

18. Apparatus according to claim 17, wherein said neutralization chamber is a pressure chamber.

19. Apparatus according to claim 17, wherein said neutralization chamber is suitable for operating at temperature of about 100° C. to 171° C.

20. Apparatus according to claim 19 wherein a plurality of temperature sensors are disposed inside said neutralization chamber for measuring the temperature of the shredded waste and air inside said chamber.

21. Apparatus according to claim 17, wherein said neutralization chamber further comprises a cyclone cavity for separating shredded waste from influx of air and shredded waste transported into the neutralization chamber.

22. Apparatus according to claim 21, wherein said radio-frequency heater applicator comprises a ground electrode, a heater electrode, and an insulator disk of sufficient thickness to prevent radio-frequency energy from leaking from said neutralization chamber.

23. Apparatus according to claim 22, wherein said ground electrode comprises an outer tubular shell, an inner tubular shell, and a middle tubular shell disposed between said inner and outer shells, said middle shell comprising an electrically conductive metal.

24. Apparatus according to claim 23 wherein said means for transporting shredded waste is a pneumatic conveyor.

25. Apparatus according to claim 24 wherein said pneumatic conveyor comprises hoppers for collecting waste, a helix conveying screw mounted within said hopper for pushing waste out of said hopper, a discharge nozzle disposed at an outlet of said hopper, and a blower disposed at an inlet of said hopper for providing continuous flow of air into said hopper.

26. Apparatus according to claim 22 wherein said heater electrode comprises a dielectric insulating material, and a conductor tube connected to a source of radio-frequency electricity.

27. Apparatus according to claim 22 wherein said insulator disk contains at least one escapement hole oriented in the axial direction to said neutralization chamber to provide a passageway for removal of neutralized waste from said neutralization chamber.

28. Apparatus according to claim 17, wherein said sealable cover has an opening therein for passing biohazardous waste therethrough into said loading chamber to prevent escape of air or biohazardous waste from said chamber.

29. Apparatus according to claim 17 further including sensors for sensing at least one of either of flow of biohazardous waste into said loading chamber, rate of shredding of the biohazardous waste in said shredders, or rate of loading of shredded waste into said neutralization chamber.

30. Apparatus according to claim 17 further including an electronic scanning device for scanning bar code labels mounted on said containers.

31. Apparatus according to claim 30 further including a radiation detector for sensing radioactive material in said biohazardous waste in said containers.

* * * * *